United States Patent
Cordi et al.

[11] Patent Number: 5,648,374
[45] Date of Patent: *Jul. 15, 1997

[54] BENZOSPIROALKENE COMPOUNDS

[75] Inventors: Alex Cordi, Suresnes; Jean-Michel Lacoste, Sevres; Michel Laubie, Vaucresson; Tony Verbeuren, Vernouillet; Jean-Jacques Descombes, Neuilly-Plaisance; Mark Millan, Paris, all of France

[73] Assignee: ADIR et Compagnie, Courbevoie, France

[*] Notice: The term of this patent shall not extend beyond the expiration date of Pat. No. 5,464,859.

[21] Appl. No.: 420,064

[22] Filed: Apr. 11, 1995

Related U.S. Application Data

[62] Division of Ser. No. 276,910, Jul. 19, 1994, Pat. No. 5,486,532.

Foreign Application Priority Data

Jul. 20, 1993 [FR] France ................... 93 08859

[51] Int. Cl.$^6$ ........................... C07D 263/28
[52] U.S. Cl. ................... 514/401; 548/301.1
[58] Field of Search ............ 548/301.1; 541/401

[56] References Cited

U.S. PATENT DOCUMENTS 5,436,261  7/1995  Cordi et al. ............. 548/301.1
5,464,859  11/1995 Cordi et al. ............. 548/301.1

*Primary Examiner*—Donald Daus
*Attorney, Agent, or Firm*—The Firm of Gordon W. Hueschen

[57] ABSTRACT

Compounds of formula (I):

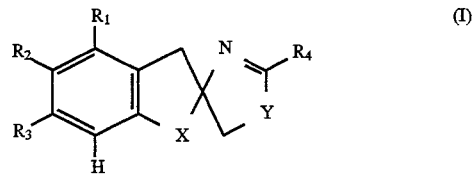

in which:

X represents —CH$_2$—, —(CH$_2$)$_2$—, —CH=CH—, —O—CH$_2$—, —S—CH$_2$—, —SO—CH$_2$— or —SO$_2$—CH$_2$—, Y represents oxygen or sulfur or —NR$_5$—, R$_1$ represents halogen, linear or branched (C$_1$-C$_6$) alkyl (unsubstituted or substituted), hydroxyl or linear or branched (C$_1$-C$_6$) alkoxy, R$_2$ represents hydrogen or halogen, linear or branched (C$_1$-C$_6$) alkyl (unsubstituted or substituted), hydroxyl, linear or branched (C$_1$-C$_6$) alkoxy or linear or branched (C$_1$-C$_6$) alkylthio, R$_3$ represents hydrogen or halogen, linear or branched (C$_1$-C$_6$) alkyl (unsubstituted or substituted), hydroxyl, linear or branched (C$_1$-C$_6$) alkoxy or linear or branched (C$_1$-C$_6$) alkylthio, R$_4$ represents hydrogen or amino (unsubstituted or substituted)

R$_5$ represents hydrogen or linear or branched (C$_1$-C$_6$) alkyl, or alternatively R$_1$ and R$_2$ form, together with the carbon atoms which bear them, a benzenic ring, on condition that, in this case, X represents —CH$_2$— or —(CH$_2$)$_2$—, their isomers and their addition salts with a pharmaceutically acceptable acid, and medicinal product containing the same are useful as α2-adrenergic agonist.

5 Claims, No Drawings

BENZOSPIROALKENE COMPOUNDS

The present application is division of our prior-filed application Ser. No. 08/276,910, filed Jul. 19, 1994, now U.S. Pat. No. 5,486,532.

The present invention relates to novel benzospiroalkenes.

The adrenergic nervous system plays an important role at several levels, for example at the arterial, venous, cardiac and renal levels and in the central and peripheral autonomic nervous system. Hence, products capable of interacting with the adrenergic receptors may induce a large number of physiological responses, such as vasoconstriction, vasodilation, increasing or decreasing the heart rate, varying the force of contraction of the cardiac muscles and varying metabolic activities. Various adrenergic compounds have been used in the past to modify these physiological or other responses.

Adrenergic stimulation in the peripheral nervous system is therapeutically useful when a vascular constriction takes place, such as in nasal, optic or ophthalmic congestions and in inflammation. Adrenergic stimulation in the central nervous system is particularly useful for inducing analgesia, anesthesia and diuresis, as well as for treating hypertension and the symptoms of withdrawal from opiates. These effects are described in particular by P. Timmermans et al. in "Comprehensive Medicinal Chemistry" (Vol. III, p. 134–185, 1990-C. Hansh editor, Pergamon, Oxford).

Besides the fact that they are new, the compounds described in the present invention possess an $_2$-adrenergic agonist profile which makes them useful, as indicated among others by P. Timmermans et al. (J. Med. Chem., 25, No. 12, 1389–1401, 1982) or S. Munk et al., (Bioorg. & Med. Chem. Lett., 4, No. 3, 459–462, 1994), as inhibitors of overactivation of the central nervous routes which are thought to contribute to anxiety and to panic attacks, as anesthetics (in order to reduce the need for inhalation agents and to promote hemodynamic stability without respiratory depression), as analgesics (more particularly in the treatment of neuropathic pain), and as hypotensive agents, sedatives, vasoconstrictors, decongestants, ocular hypotensive agents and for overcoming opiate withdrawal symptoms. The therapeutic use of the products of the invention is based on their selectivity for the adrenergic receptors and their selective modulation of the adrenergic functions in various tissues and organs.

The present invention more specifically relates to the compounds of formula (I):

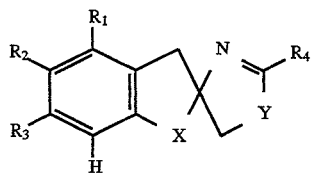

in which:

X represents —$CH_2$—, —$(CH_2)_2$—, —CH=CH—, —O—$CH_2$—, —S—$CH_2$—, —SO—$CH_2$— or —$SO_2$—$CH_2$—, Y represents an oxygen or sulfur atom or a group —$NR_5$—, $R_1$ represents a halogen atom, a linear or branched ($C_1$–$C_6$) alkyl group (unsubstituted or substituted with one or more halogen atoms), a hydroxyl group or a linear or branched ($C_1$–$C_6$) alkoxy group, $R_2$ represents a hydrogen or halogen atom, a linear or branched ($C_1$–$C_6$) alkyl group (unsubstituted or substituted with one or more halogen atoms), a hydroxyl group, a linear or branched ($C_1$–$C_6$) alkoxy group or a linear or branched ($C_1$–$C_6$) alkylthio group, $R_3$ represents a hydrogen or halogen atom, a linear or branched ($C_1$–$C_6$) alkyl group (unsubstituted or substituted with one or more halogen atoms), a hydroxyl group, a linear or branched ($C_1$–$C_6$) alkoxy group or a linear or branched ($C_1$–$C_6$) alkylthio group, $R_4$ represents a hydrogen atom or an amino group (unsubstituted or substituted with one or two linear or branched ($C_1$–$C_6$) alkyl groups), $R_5$ represents a hydrogen atom or a linear or branched ($C_1$–$C_6$) alkyl group, or alternatively $R_1$ and $R_2$ form, together with the carbon atoms which bear them, a benzenic ring, on condition that, in this case, X represents —$CH_2$— or —$(CH_2)_2$—, their isomers and their addition salts with a pharmaceutically acceptable acid.

Among the pharmaceutically acceptable acids there may, in a non-limiting manner, be mentioned hydrochloric, hydrobromic, sulfuric, phosphoric, acetic, lactic, malonic, succinic, fumaric, tartaric, maleic, citric, methanesulfonic acids and the like.

Among the possible isomers of the compounds of formula (I) there may be mentioned the enantiomers, the diastereomers, the epimers and the tautomers.

The invention also covers the process for the preparation of the compounds of formula (I).

The compounds of formula (I) for which Y represents a group —$NR_5$ are obtained according to the process wherein the starting material used is a compound of formula (II):

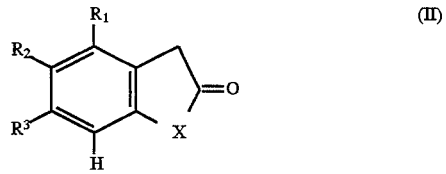

in which X, $R_1$, $R_2$ and $R_3$ have the same meaning as in formula (I) which is reacted:

either with benzylamine in the presence of para-toluenesulfonic acid in order to lead to the compound of formula (III):

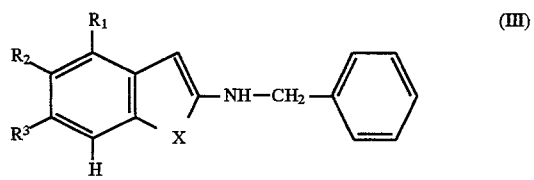

in which X, $R_1$, $R_2$ and $R_3$ have the same meaning as in formula (I) which is reacted, under inert atmosphere, with trimethylsilyl cyanide in the presence of zinc iodide, in order to lead to the compound of formula (IV):

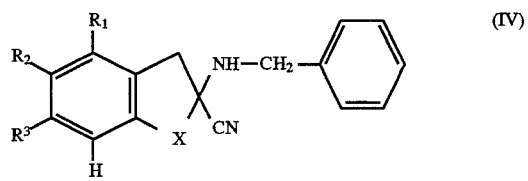

in which X, $R_1$, $R_2$ and $R_3$ have the same meaning as in formula (I), which is reduced using lithium aluminum hydride and then by catalytic hydrogenation, in order to lead to the compound of formula (V):

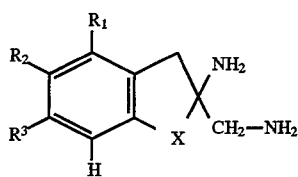

in which X, $R_1$, $R_2$ and $R_3$ have the same meaning as in formula (I), or with potassium cyanide in the presence of ammonium chloride in an inert medium or with sodium cyanide in an acidic medium, or alternatively with trimethylsilyl cyanide in the presence of zinc iodide and then with saturated alcoholic ammonia solution, in order to lead to the compound of formula (VI):

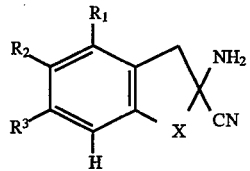

in which X, $R_1$, $R_2$ and $R_3$ have the same meaning as in formula (I), which is reduced using lithium aluminum hydride, in order to lead to the compound of formula (V) described above, which compound of formula (V) is reacted with formamidine in an alcoholic medium, an alkyl formate or with a cyanogen halide (followed, depending on the nature of the compound of formula (I) which it is desired to obtain, by an alkylation reaction using an alkyl halide), in order to lead to the compound of formula (I/a), which is a specific case of the compounds of formula (I):

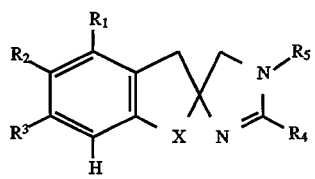

in which X, $R_1$, $R_2$, $R_3$, $R_4$ and $R_5$ have the same meaning as in formula (I), which compound of formula (I/a) is purified, where appropriate, according to a standard purification technique, and for which, if so desired, the isomers are separated according to a standard purification technique, and are optionally converted to their addition salts with a pharmaceutically acceptable acid.

The compounds of formula (I) for which Y represents an oxygen or sulfur atom are obtained according to the process wherein a compound of formula (VI) described above is used as starting material, which is reacted with formic acid in a saturated an- hydrous hydrochloric acid medium, in order to lead to the compound of formula (VII):

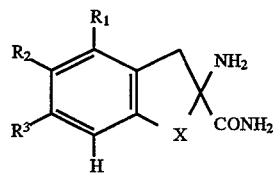

in which $R_1$, $R_2$, $R_3$ and X have the same meaning as in formula (I), which is converted to the corresponding acid of formula (VIII) in a concentrated hydrochloric medium:

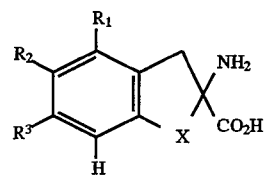

in which $R_1$, $R_2$, $R_3$ and X have the same meaning as in formula (I), which undergoes reduction by lithium aluminum hydride in an inert medium in order to lead to the compound of formula (IXa):

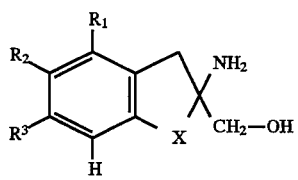

in which $R_1$, $R_2$, $R_3$ and X have the same meaning as in formula (I), which compound of formula (IXa) is converted, depending on the nature of the compounds of formula (I) which it is desired to obtain, to the corresponding tosylate using p-toluenesulfonic acid and which is then reacted with thiourea or thioacetic acid, in order to lead, after hydrolysis, to the compound of formula (IXb):

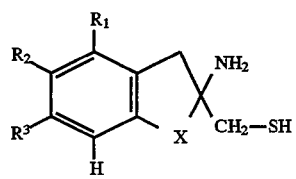

in which $R_1$, $R_2$, $R_3$ and X have the same meaning as in formula (I), which compound of formula (IXa) or (IXb) is reacted with formamidine in an alcoholic medium, an alkyl formate or with a cyanogen halide (followed, depending on the nature of the compound of formula (I) which it is desired to obtain, by an alkylation reaction using an alkyl halide), in order to lead to the compound of formula (I/b), which is a specific case of the compounds of formula (I):

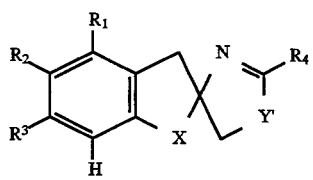

in which $R_1$, $R_2$, $R_3$ and X have the same meaning as above and Y' represents an oxygen or sulfur atom, which compound of formula (I/b) is purified, where appropriate, according to a standard purification technique, and for which, if so desired, the isomers are separated according to a standard purification technique, and are optionally converted to their addition salts with a pharmaceutically acceptable acid.

When the compounds of formula (I) which it is desired to obtain possess a hydroxyl group at $R_1$, $R_2$ or $R_3$, a preferred process for obtaining these compounds consists in synthesizing, in a first step, the derivative of formula (I) possessing an alkoxy group at $R_1$, $R_2$ or $R_3$, which is convened to the corresponding hydroxyl group by the action of boron tribromide in dichloromethane medium.

Another subject of the present invention is the pharmaceutical compositions containing as active principle at least one compound of general formula (I) or one of its addition salts with a pharmacologically acceptable acid, alone or in combination with one or more inert, non-toxic excipients or vehicles.

Among the pharmaceutical compositions according to the invention, there may more particularly be mentioned those which are suitable for oral, parenteral and nasal administration, simple or sugar-coated tablets, sublingual tablets, gelatin capsules, lozenges, suppositories, creams, ointments, dermal gels and the like.

The dosage varies depending on the age and weight of the patient, the nature and severity of the complaint and the route of administration.

The latter may be oral, nasal, rectal or parenteral. Generally speaking, the unit dose is graded between 0.1 and 1000 mg for a treatment, taken 1 to 3 times per 24 hours.

The examples which follow illustrate the invention. The starting materials used are known products or are prepared according to known experimental procedures.

EXAMPLE 1

Spiro[(1,3-diazacyclopent-1-ene)-5:2'-(8'-chloro-1',2',3', 4'-tetrahydro naphthalene)]fumarate Stage A:

2-Amino-2-cyano-8-chloro-1,2,3,4-tetrahydronaphthalene

To a vigorously stirred solution, maintained under nitrogen, containing 43 mmol of 8-chloro-3,4-dihydro-2 (1H)-naphthalenone in 60 ml of ethanol and 30 ml of water are successively added 44 mmol of potassium cyanide and 44 mmol of ammonium chloride. After stirring for 20 hours at 20° C., the mixture is concentrated under vacuum and the residue is taken up in 80 ml of ethyl acetate. This organic phase is washed with water and is then extracted with 1N hydrochloric acid. The aqueous phase is basified with 35% sodium hydroxide and extracted with ethyl acetate. The expected product is obtained after drying and evaporation of the organic phase as a solid.

Melting point: 67°–69° C.

Stage B:

2-Amino-2-aminomethyl-8-chloro-1,2,3,4-tetrahydronaphthalene

To a suspension containing 43 mmol of lithium aluminum hydride in 50 ml of tetrahydrofurane is added dropwise a solution containing 19 mmol of the compound obtained in the preceding stage, while maintaining a temperature which does not exceed 20° C. The mixture is stirred for 30 minutes, cooled to 0° C. and then hydrolyzed by addition of 1.6 ml of water, 1.6 ml of 2N sodium hydroxide and then 3.5 ml of water. The resultant suspension is filtered and the filtrate evaporated to give the expected product in oil form.

Stage C:

Spiro [(1,3-diazacyclopent-1-ene)-5:2'-(8'-chloro-1',2',3', 4'-tetrahydro naphthalene)]fumarate A mixture containing 14 mmol of the compound obtained in the preceding stage and 14 ml of formamidine acetate in 60 ml of ethanol is stirred at 20° C. under a nitrogen atmosphere for 10 hours. The solvent is then evaporated off and the residue is taken up in 1N hydrochloric acid. This acidic phase is washed with ethyl acetate and basified with 35% sodium hydroxide. The mixture is then extracted with ethyl acetate and the organic phase is washed with saturated sodium chloride solution and evaporated. The solid residue thus obtained is dissolved in 20 ml of ethanol and treated with one equivalent of fumaric acid dissolved in ethanol.

After evaporation of the solvent, the expected product is obtained by recrystallization of the residue in ethanol.

Melting point: 213°–215° C.

| | Elemental microanalysis: | | | |
|---|---|---|---|---|
| | C % | H % | N % | Cl % |
| calculated | 57.06 | 5.09 | 8.32 | 10.53 |
| found | 56.88 | 5.21 | 8.30 | 10.47 |

The expected products of Examples 2, 3 and 4 were synthesized according to the process described in Example 1, using the corresponding starting materials.

EXAMPLE 2

Spiro[(1,3-diazacyclopent-1-ene)-5:2'-(8'-fluoro-1',2',3', 4'-tetrahydronaphthalene)]fumarate Melting point: 187°–190° C.

| | Elemental microanalysis: | | |
|---|---|---|---|
| | C % | H % | N % |
| calculated | 60.00 | 5.35 | 8.75 |
| found | 59.89 | 5.60 | 8.46 |

EXAMPLE 3

Spiro[(1,3-diazacyclopent-1-ene)-5:2'-(8'-methoxy-1',2', 3',4'-tetrahydronaphthalene)]fumarate Melting point: 186°–188° C.

| | Elemental microanalysis: | | |
|---|---|---|---|
| | C % | H % | N % |
| calculated | 61.44 | 6.07 | 8.43 |
| found | 61.30 | 5.90 | 8.55 |

EXAMPLE 4

Spiro[(1,3-diazacyclopent-1-ene)-5:2'-(6',8'-dichloro-1', 2',3',4'-tetrahydronaphthalene)]fumarate Melting point: 194°–195° C.

| | Elemental microanalysis: | | | |
|---|---|---|---|---|
| | C % | H % | N % | Cl % |
| calculated | 51.77 | 4.34 | 7.55 | 19.10 |
| found | 51.80 | 4.37 | 7.43 | 18.54 |

EXAMPLE 5

Spiro[(1,3-diazacyclopent-1-ene)-5:2'-(8'-hydroxy-1',2', 3',4'-tetrahydronaphthalene)]fumarate To a solution, maintained under nitrogen, containing 4.5 mmol of the compound describe in Example 3 in 30 ml of dichloromethane are added dropwise 16.6 ml of a 1M solution of boron tribromide in dichloromethane. The temperature of the reaction medium is brought to 20° C. and the mixture is then poured into chilled sodium bicarbonate solution. After evaporation of the aqueous phase, the residue is taken up in isopropanol. The solvent is evaporated off and the oil obtained is purified by chromatography on a column of silica, using a water/dioxane/aqueous ammonia mixture (90/10/1) as eluent. The solid isolated is dissolved in ethanol and treated with one equivalent of fumaric acid dissolved in ethanol. The expected product is obtained after evaporation and recrystallization of the residue in ethanol.
Melting point: 240°–242° C.

| | Elemental microanalysis: | | |
|---|---|---|---|
| | C % | H % | N % |
| calculated | 64.60 | 6.20 | 10.76 |
| found | 63.95 | 6.11 | 10.58 |

EXAMPLE 6

Spiro[(1,3-diazacyclopent-1-ene)-5:2'-(8'-chloro-1',2',3',4'-tetrahydronaphthalene)]L-(+)-tartrate, α isomer The compound of Example 1 is resolved using L-(+)-tartaric acid by successive recrystallizations in methanol. The enantiomeric purity is verified by chromatography on an $_1$-AGP chiral column, using an $Na_2HPO_4$aq.0.01M/$NaH_2PO_4$aq.0.01M/n-propanol mixture (60/40/1) as eluent.
Melting point: 218°–221° C.

| | Elemental microanalysis: | | | |
|---|---|---|---|---|
| | C % | H % | N % | Cl % |
| calculated | 51.83 | 5.16 | 7.56 | 9.56 |
| found | 51.27 | 5.02 | 7.54 | 9.56 |

EXAMPLE 7

Spiro[(1,3-diazacyclopent-1-ene)-5:2'-(8'-chloro-1',2',3',4'-tetrahydronaphthalene)]D-(−)tartrate, β isomer The expected product is obtained according to the process described in Example 6, from the compound of Example 1 and D-(−)-tartaric acid.
Melting point: 218°–221° C.

| | Elemental microanalysis: | | | |
|---|---|---|---|---|
| | C % | H % | N % | Cl % |
| calculated | 51.83 | 5.16 | 7.56 | 9.56 |
| found | 51.88 | 5.16 | 7.64 | 9.64 |

EXAMPLE 8

Spiro[(1,3-diazacyclopent-1-ene)-5:3'-(1',2',3',4'-tetrahydrophenanthrene)]fumarate
Stage A:
3-Amino-3-cyano-1,2,3,4-tetrahydrophenanthrene To a stirred mixture containing 13 mmol of 1,2-dihydro-3(4H)-phenanthrenone and 40 mmol of sodium cyanide in 70 ml of water and 10 ml of ethyl ether is added dropwise 1 ml of concentrated hydrochloric acid. After stirring for 1 hour at 20° C., the organic phase is separated out after settling has taken place, washed with water, dried and concentrated under vacuum. The residual oil is treated with 20 ml of methanolic ammonia solution (3.5M), with stirring, in a closed medium, for 4 hours at 20° C. After evaporation of the solvent, the oil obtained is taken up in 30 ml of ethyl ether and extracted with 1N hydrochloric acid. The aqueous phase is basified with 35% sodium hydroxide and is then extracted with ethyl ether. After drying and evaporating, the expected product is obtained in solid form.
Melting point: 75°–78° C.
Stage B:
3-Amino-3-aminomethyl-1,2,3,4-tetrahydrophenanthrene The expected product is obtained according to the process described in stage B of Example 1, from the compound described in the preceding stage.
Stage C:
Spiro[(1,3-diazacyclopent-1-ene)-5:3'-(1',2',3',4'-tetrahydrophenanthrene)]fumarate The expected product is obtained according to the process described in stage C of Example 1, from the compound described in the preceding stage.
Melting point: 212°–215° C.

| | Elemental microanalysis | | |
|---|---|---|---|
| | C % | H % | N % |
| calculated | 68.17 | 5.72 | 7.95 |
| found | 67.78 | 5.63 | 7.93 |

EXAMPLE 9

Spiro[(1-oxa-2-amino-3-azacyclopent-2-ene)-4:2'-(8'-chloro-1',2',3',4'-tetrahydrophenanthrene)]hydrochloride
Stage A:
2-Amino-2-cyano-8-chloro-1,2,3,4-tetrahydronaphthalene To a vigorously stirred solution, maintained under nitrogen, containing 277 mmol of 8-chloro-3,4-dihydro-2 (1H)-naphthalenone in 350 ml of methanol and 170 ml of water are successively added 282 mmol of potassium cyanide and 290 mmol of ammonium chloride. After stirring for 48 hours at 20° C., the mixture is concentrated. The residue is taken up in ethyl acetate. This organic phase is washed with water and extracted with 1N hydrochloric acid. The acidic phases are basified with 35% sodium hydroxide and extracted with ethyl acetate. The expected product is obtained, in solid form, after drying and evaporating the organic phases.
Melting point: 67°–69° C.
Stage B:
2-Amino-2-aminocarbonyl-8-chloro-1,2,3,4-tetrahydronaphthalene hydrochloride A solution containing 114 mmol of the compound obtained in the preceding stage in 110 ml of formic acid is cooled to 0° C. and saturated with anhydrous hydrogen chloride acid gas for 3 hours. The mixture is then stirred at 20° C. for 16 hours, the solvent is evaporated off and the residue is taken up in 150 ml of acetone. The expected product is obtained by filtration of the crystallized white solid.
Stage C:
2-Amino-8-chloro-1,2,3,4-tetrahydronaphthalene-2-carboxylic acid A suspension containing 79 mmol of the compound obtained in the preceding stage in 125 ml of 6N hydrochloric acid is brought to reflux until complete dissolution is achieved. The solvent is then evaporated off, the residue is taken up in isopropanol and the pH of the solution is brought to 7 by the addition of 1N sodium hydroxide. The expected product is obtained after filtering and drying the precipitated white solid.

Stage D:

2-Amino-2-hydroxymethyl-8-chloro-1,2,3,4-tetrahydronaphthalene

To a solution containing 35.4 mmol of the compound obtained in the preceding stage in 100 ml of tetrahydrofuran (THF) is added dropwise, under a nitrogen atmosphere and at room temperature, a suspension of 79 mmol of lithium aluminum hydride in 150 ml of anhydrous THF. The mixture is brought to reflux for 1 hour. After cooling to 0° C., the medium is hydrolyzed by successive addition of 3 ml of water, 3 ml of 2.5N sodium hydroxide and 6 ml of water. The white solid formed is filtered off and washed with THF. The expected product is obtained in oil form after concentration of the filtrates under vacuum.

Stage E:

Spiro[(1-oxa-2-amino-3-azacyclopent-2-ene)-4:2'-(8'-chloro-1',2',3',4'-tetrahydronaphthalene)]hydrochloride A solution containing 33.5 mmol of cyanogen bromide in 15 ml of dichloromethane is added, at 0° C., to a solution containing 29.5 mmol of the compound obtained in the preceding stage in 60 ml of dichloromethane. The mixture is stirred for 16 hours at 20° C. and the solid formed is then filtered off and washed with dichloromethane. The filtrates are washed with potassium bicarbonate solution, dried and evaporated. The expected product is obtained by purification of the residue by chromatography on a column of silica, using a dichlomethane/ethanol/aqueous ammonia mixture (92.5/7/0.5) as eluent. The oil obtained is taken up in ethyl ether and treated with hydrochloric ether solution (4N). The precipitate formed is filtered off and recrystallized in an isopropanol/ethyl ether mixture.

Melting point:
210°–214° C.

| | Elemental microanalysis: | | | |
|---|---|---|---|---|
| | C % | H % | N % | Cl % |
| calculated | 52.76 | 5.17 | 10.26 | 25.96 |
| found | 52.99 | 5.10 | 10.16 | 25.71 |

EXAMPLE 10

Spiro[(1-oxa-2-amino-3-azacyclopent-2-ene)-4:2'-(7-8'-dichloro-1',2',3',4'-tetrahydronaphthalene)]hydrochloride The expected product is obtained according to the process described in Example 9, using the corresponding starting material.

Melting point: <260° C.

| | Elemental microanalysis: | | | |
|---|---|---|---|---|
| | C % | H % | N % | Cl % |
| calculated | 46.86 | 4.26 | 9.11 | 34.58 |
| found | 46.63 | 4.45 | 8.89 | 34.97 |

EXAMPLE 11

Spiro[(1-oxa-2-amino-3-azacyclopent-2-ene)-4:2'-(7-8'-dimethyl-1',2',3',4'-tetrahydronaphthalene)]hydrochloride The expected product is obtained according to the process described in Example 9, using the corresponding starting material.

Melting point: 246°–249° C.

| | Elemental microanalysis: | | | |
|---|---|---|---|---|
| | C % | H % | N % | Cl % |
| calculated | 63.03 | 7.18 | 10.50 | 13.29 |
| found | 62.00 | 7.03 | 10.31 | 13.08 |

EXAMPLE 12

Spiro[(1-oxa-2-amino-3-azacyclopent-2-ene)-4:2'-(8'-chloro-1',2',3',4'-tetrahydronaphthalene)]hydrochloride, α isomer Stage A:

2-Amino-8-hydroxymethyl-8-chloro-1,2,3,4-tetrahydronaphthalene fumarate, α isomer The expected product is obtained by resolving the compound obtained in stage D of Example 9 using (+)-dibenzoyl-D-tartaric acid by successive recrystallizations in ethanol. The enantiomeric purity is checked by chiral chromatography on a DIACEL-AD column, using an isopropanol/n-heptane/diethylamine mixture (40/1000/0.8) as eluent. The salt is then partitioned between 9N sodium hydroxide and dichloromethane. The aqueous phase is extracted with dichloromethane. After drying and evaporating the organic phases, the residue is dissolved in ethanol with one equivalent of fumaric acid and the mixture is brought to reflux. The expected product is then obtained after cooling, in the form of a white solid which is filtered off.

Stage B:

Spiro[(1-oxa-2-amino-3-azacyclopent-2-ene)-4:2'-(8'-chloro-1',2',3',4'-tetrahydronaphthalene)]hydrochloride, α isomer The expected product is obtained according to the process described in stage E of Example 9, from the compound obtained in the preceding stage.

Melting point: 212°–214° C.

| | Elemental microanalysis: | | | |
|---|---|---|---|---|
| | C % | H % | N % | Cl % |
| calculated | 52.76 | 5.17 | 10.26 | 25.96 |
| found | 52.09 | 5.18 | 10.01 | 25.88 |

EXAMPLE 13

Spiro[(1-oxa-2-amino-3-azacyclopent-2-ene)-4:2'-(8'-chloro-1',2',3',4'-tetrahydronaphthalene)]hydrochloride, β isomer Stage A:

2-Amino-8-hydroxylmethyl-8-chloro-1,2,3,4-tetrahydronaphthalene fumarate, β isomer The expected product is obtained according to the process described in stage A of Example 12, using (−)-dibenzoyl-L-tartaric acid for the resolution.

Stage B:

Spiro[(1-oxa-2-amino-3-azacyclopent-2-ene)-4:2'-(8'-chloro-1',2',3',4'-tetrahydronaphthalene)]hydrochloride, β isomer The expected product is obtained according to the process described in stage E of Example 9, from the compound obtained in the preceding stage.

Melting point: 212°–214° C.

Elemental microanalysis:

|  | C % | H % | N % | Cl % |
|---|---|---|---|---|
| calculated | 52.76 | 5.17 | 10.26 | 25.96 |
| found | 52.51 | 5.20 | 10.03 | 25.62 |

Pharmacological Study of the Compounds of the Invention

EXAMPLE 14

In Vitro Study on Dog Femoral Arteries and Saphena Veins

The technique used is based on that described by Fowler et al. (J. Pharmacol. Exp. Ther., 229, 712–718, 1984). Male or female mongrel dogs of approximately 15–25 kg were used as organ sources. The animals are anesthetized with pentobarbital (30 mg/kg intravenously). The legs are incized and the blood vessels removed. They are placed in Krebs-Ringer liquid (118 mM NaCl; 25 mM $NaHCO_3$; 10 mM Glucose; 4.7 mM KCl; 1.25 mM $CaCl_2$; 1.19 mM $MgSO_4$; 1.14 mM $KH_2PO_4$) at room temperature and under a sparge of carbogen (95% $O_2$, 5% $CO_2$). These blood vessels are then carefully freed of their fat and then cut into rings 2 mm wide and mounted under a base tension of 4 g (femoral arteries) or 1 g (saphena veins) in tanks thermostated at 37° C. containing Krebs-Ringer liquid and constantly sparged with carbogen. A lower hook constitutes the fixed point, whereas the upper hook is connected to an isometric force sensor. The variations in tension are digitized, stored on disk and processed by an information technology system. After mounting, the organs are left to rest for 90 minutes, with rinses being carried out every 30 min. After readjustment of the base tension, a contraction is induced by a single dose of KCl (100 mM). After stabilization, washing and returning to the base line, a contraction is provoqued by a single dose of phenylephrine (submaximal concentration) in order to regulate the following contractions. After washing and returning to the baseline, an effect/concentration curve is produced by addition of cumulative doses of agonist (the space between the doses is a semi-log). This experiment makes it possible to calculate the 50% effective concentration ($EC_{50}$) in the following way: the tension values are first of all converted to percentages relative to the maximum effect induced by 100 mM of KCl. This $EC_{50}$ is determined by non-linear regression by the SIMPLEX method (M. S. Caceci, Byte, 340–362, 1984), calculated according to the mass action law model of L. Michaelis and M. L. Menten (Biochem. Zeitschrift, 49, 333–369, 1913).

$E=(E_{max}*C^n)EC^n+C^n)$ with E=effect; $E_{max}$=maximum effect;

C=concentration; EC=$EC_{50}$; n=Hill number

The products of the invention contract dog arteries and veins. The maximum for these contractions approaches that obtained with KCl. The results obtained are given in the table below:

|  | ARTERY | | VEIN | |
|---|---|---|---|---|
| Example | $EC_{50}$ (µM) | Max (% KCl) | $EC_{50}$ (µM) | Max (% KCl) |
| 1 | 1 | 94 | 0.2 | 95 |
| 3 | 3 | 94 | 0.4 | 100 |
| 6 | 2 | 91 | 7 | 96 |

EXAMPLE 15

In Vivo Study in Amyelated Rats

Male Sprague Dawley rats (300–400 g) are anesthetized with ether. The trachea is cannulated, the spinal column is destroyed using a stainless-steel rod and the animal is immediately placed under artificial respiration. The vagus nerves are dissected. The carotid arteries are ligatured and a catheter is placed in one and serves to record the arterial pressure. Three other catheters are placed in the jugular veins and in the vein of the penis and serve for the injections. The temperature of the animals is maintained at 36° C. The animal is pretreated by an injection of tertatolol (100 g/kg). The animal is also pretreated 10 minutes later with prazosin (100 g/kg) or yohimbine (1 mg/kg) when it is desired to determine the $alpha_1$- or $alpha_2$-adrenergic properties of the product. Ten minutes later, increasing cumulative doses of product are injected every 20 seconds. The variations in arterial pressure are detected using a Statham P23XL pressure cell and are recorded. The pressure values are expressed in mmHg. This experiment makes it possible to calculate the concentration which increases the pressure by 20 mmHg ($C_{20}$) by non-linear regression according to the mass action law model of Michaelis and Menten as described above. The maximum effect obtained is subsequently converted to a percentage relative to the maximum effect induced by phenylephrine. The $alpha_1$- or alpha2-adrenergic components of the product are evaluated using the $C_{20}$ ratio obtained in the presence of prazosin or yohimbine on the values obtained in the absence of these antagonists. In amyelated rats, the products of the invention produce hypertensions which are sensitive to prazosin and to yohimbine. The results are given in the table bellow:

|  | $C_{20}$ (µg/kg) | Ratio treated $C_{20}$/control $C_{20}$ | |
|---|---|---|---|
| Example | Control | Prazosin | Yohimbine |
| 1 | 0.2 | 1.9 | 6.0 |
| 5 | 4.8 | 0.9 | 12.0 |
| 6 | 0.1 | 1.7 | 4.0 |

EXAMPLE 16

Effect of $\alpha_2$-Adrenergic Ligands on the Synthetic Activity of Noradrenaline in Rat Hippocampus 200–220 g male Wistar rats Iffa Credo, Illskischen, France) are individually installed in cages with free access to food and drinking water. The laboratory temperature is 21 1° C. and the percent humidity is 60 5%. The day/night cycle is 12 hours (light switched on in the morning at 7.30).

Neurochemical Analysis

The effects of the molecules on the rate of regeneration of noradrenaline is determined 60 minutes after their administration via the subcutaneous route. The activity of the compounds of the invention is compared to the activity of an $\alpha_2$-agonist of reference: UK 14,304 (Life Sciences, vol. 43, n°22, 1805–1812, 1988). Thirty minutes before the sacrifice, the animals receive an inhibitor of the decarboxylation enzyme, NSD 1015 (100 mg/kg s.c.). The animals are then decapitated, their brain is removed and the hippocampus is dissected. The hippocampus is subsequently homogenized in 500 1 of 0.1M $HClO_4$ containing 0.5% of $Na_2S_2O_5$ and 0.5% of disodium EDTA and centrifuged at 15000 g for 15 minutes at 4° C. In order to measure the amounts of L-dihydroxyphenylalanine (L-DOPA), the precursor of noradrenaline, present, the supernatants are diluted 20 times in the chromatography mobile phase and 100 1 are analyzed by high performance liquid chromatography with electrochemical detection (Waters M460 detector, potential of the working electrode:850 mV). The column (Hypersil ODS 5 m, C18, 150 4.6 mm, Spectra Physics) is thermostatted at 25° C. The mobile phase is composed of 100 mM of $KH_2PO_4$, 0.1 mM of $Na_2EDTA$, 0.5 mM of sodium octylsulfonate and 5% of methanol and adjusted to pH 3.15 with concentrated $H_3PO_4$. The flow rate is 1 ml/min. The amounts of L-DOPA are determined relative to an external calibration and are compared with the amount of protein present in the hippocampi. The proteins are quantified according to the method of Smith et al. (Anal. Biochem., 150, 76–85, 1985) using bovine serum albumin as standard (Sigma Chemical Co., St. Louis, Mo.). The average amount of L-DOPA analyzed in the animals treated by the solvent is considered as the control value (100%). The amounts analyzed in the animals treated by the molecules are then expressed as a percentage relative to this control value.

Statistics

The data obtained for the control animals and the treated animals are compared with a variance analysis (ANOVA), followed by a Dunnett test. The significance limit is set at $p>0.05$. The data are expressed as a mean standard deviation.

Compounds

The injection are made subcutaneously in a volume of 1.0 ml/kg. The substances are dissolved in sterile water with, if necessary, a few drops of lactic acid and then readjusted to a pH which is as close as possible to neutrality with sodium hydroxide. NSD-1015 is dissolved in physiological serum. The doses are expressed relative to their weight of free base.

The results obtained for the compound of Example 9 and UK 14,304 are given below:

|  | Dose (mg/kg) | Accumulation of L-DOPA Control percentages |
|---|---|---|
| Example 9 | 0.01 | 51 ± 7* (n = 4) |
|  | 0.04 | 50 ± 7* (n = 4) |
|  | 0.16 | 44 ± 2* (n = 4) |
|  | 0.63 | 34 ± 2* (n = 4) |
| UK 14,304 | 0.01 | 98 ± 13* (n = 4) |
|  | 0.04 | 70 ± 2* (n = 4) |
|  | 0.16 | 40 ± 3* (n = 4) |
|  | 0.63 | 48 ± 7* (n = 4) |
|  | Vehicle | 100 ± 5 (n = 4) |

*p < 0.05 relative to vehicle
absolute value for L-DOPA: 476.4 ± 16.8 pg/mg protein

EXAMPLE 17

Test of Loss of the Righting Reflex in Rats

Materials and Methods

Animals and Environment

The animals used are male Wistar rats (IFFA CREDO). They weigh between 200 and 250 g at the time of the experiment. The rats live in an animal house, in cages, four to a cage, with free access to food and drinking water, for one week before being studied. 24 hours before the experiment, the rats are deprived of food. The rats are transferred into the laboratory a few hours before the experiment. The animal house and the laboratory are climatically controlled at a temperature of 21 1° C. and a hygrometry of 55 5%. The lighting cycle is 12 h/12 h with the light switched on from 7.0 a.m. to 7.0 p.m. The rats are only experimented on once.

Description of the Test

The compounds are injected subcutaneously into the rats which are placed in individual cages. 30 minutes after the injection the effect of these products on the righting reflex is observed and a score is attributed. Immediately after, the rats receive an intraperitoneal injection of xylazine at a dose of 40 mg/kg. 30 minutes after the injection of xylazine (=60 minutes after the injection of the compounds to be tested), a new righting reflex score is attributed. In order to evaluate the fighting reflex, the rats are placed gently on their backs and then released. A score of 0 is attributed to an immediate and complete righting, a score of 1 to a righting without recovery of a normal position, a score of 2 to a fighting attempt but in which the rat remains stretched out on its back and a score of 3 to a complete loss of the reorienting reflex.

Assessment Criteria

In order to evaluate the effect of the compounds tested on the loss of the fighting reflex, a score of 1 or more is considered as an agonistic effect. The percentage of animals which have a score of 1 or more is calculated per dose, as is the $ED_{50}$ (=dose at which 50% of the animals show an agonistic effect).

In order to evaluate the effect of the compounds tested on the loss of the fighting reflex induced by xylazine, a score of 2 or less is considered as an antagonistic effect. The percentage of animals which have a score of 2 or less is calculated per dose, as is the $ED_{50}$ (=dose at which 50% of the animals show an antagonistic effect). The $ED_{50}$ are calculated according to Litchfield and Wilcoxon.

Products to be Tested

The products are dissolved in distilled water, or distilled water with a few drops of lactic acid in the case of solubilization difficulties. The pH of the solutions is then brought to 5 using sodium hydroxide solution. All the products are administered in a volume of 10 ml/kg.

Results 30 minutes after the subcutaneous injection of distilled water, no loss of righting reflex was observed in the control rats: mean±SD score was 0±0 (N=10). 30 minutes after the injection of xylazine (and 60 minutes after the injection of distilled water in the pretreatment), all the control rats (N=10) had lost the righting reflex: mean±SD score was 3±0. The table below shows the $ED_{50}$ values of the products tested for their capacity, respectively, to induce a loss of fighting reflex or to antagonize a loss of fighting reflex induced by xylazine. Xylazine, the reference $\alpha_2$-agonist UK 14,304 and the compounds of Examples 9, 11 and 13 behave as agonists by inducing a loss of the reorienting reflex, with the exception of idazoxan, an $\alpha_2$-antagonist which is inactiv.

| Compounds | Induction of the loss of righting reflex $ED_{50}$ | Antagonism of the loss of righting reflex induced by xylazine $ED_{50}$ |
|---|---|---|
| XYLAZINE | 6.1 | — |
| UK 14,304 | 0.24 | >10 |
| IDAZOXAN | >10.0 | 0.24 |
| Example 9 | 0.17 | >0.63 |
| Example 11 | 1.14 | >2.50 |
| Example 13 | 0.15 | >0.63 |

EXAMPLE 18

Pharmaceutical Composition
Preparation Formula for 1000 Tablets Containing 10 mg Doses

| | |
|---|---|
| Compound of Example 9 | 10 g |
| Hydroxypropylcellulose | 2 g |
| Wheat starch | 10 g |
| Lactose | 100 g |
| Magnesium stearate | 3 g |
| Talc | 3 g |

We claim:

1. A compound of formula (I):

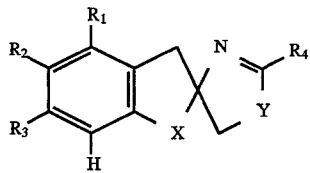

(I)

in which:

X represents —$CH_2$—, —$(CH_2)_2$—, —CH=CH—, —O—$CH_2$—, —S—$CH_2$—, —SO—$CH_2$—, or —$SO_2$—$CH_2$—, Y represents a group —$NR_5$—, $R_1$ represents halogen, linear or branched ($C_1$–$C_6$) alkyl which is unsubstituted or substituted with one or more halogen; hydroxyl, or linear or branched ($C_1$–$C_6$) alkoxy, $R_2$ represents hydrogen or halogen, linear or branched ($C_1$–$C_6$) alkyl which is unsubstituted or substituted with one or more halogen; hydroxyl, linear or branched ($C_1$–$C_6$) alkoxy, or linear or branched ($C_1$–$C_6$) alkylthio, $R_3$ represents hydrogen or halogen, linear or branched ($C_1$–$C_6$) alkyl which is unsubstituted or substituted with one or more halogen; hydroxyl, linear or branched ($C_1$–$C_6$) alkoxy, or linear or branched ($C_1$–$C_6$) alkylthio, $R_4$ represents hydrogen or amino which is unsubstituted or substituted with one or two linear or branched ($C_1$–$C_6$) alkyl;

$R_5$ represents hydrogen or linear or branched ($C_1$–$C_6$) alkyl, or alternatively $R_1$ and $R_2$ form, together with the carbon atoms which bear them, a benzenic ring, on condition that, in this case, X represents —$CH_2$— or —$(CH_2)_2$, an optical isomer thereof or an addition salt thereof with a pharmaceutically-acceptable acid, it being understood that by "halogen" is intended fluorine, chlorine, or bromine, and that substituents $R_1$, $R_2$, and $R_3$ cannot include two tertiary butyl substituents on adjacent carbon atoms of the benzene ring.

2. A compound of selected from those claim 1, wherein Y represents —NH—, an optical isomer thereof, or an addition salt thereof with a pharmaceutically-acceptable acid.

3. A compound of claim 1, which is selected from spiro[(1,3-diazacyclopent-1-ene)-5:2'-(8'-chloro-1',2',3',4'-tetrahydronaphthalene)], an optical isomer thereof, or an addition salt thereof with a pharmaceutically-acceptable acid.

4. A method for treating a mammal afflicted with a condition requiring an $\alpha_2$-adrenergic agonist, comprising the step of administering to the mammal an amount of a compound of claim 1 which is effective for alleviation of said condition.

5. A pharmaceutical composition useful as an $\alpha_2$-adrenergic agonist comprising as active principle an effective mount of a compound as claimed in claim 1, together with a pharmaceutically-acceptable excipient.

* * * * *

UNITED STATES PATENT AND TRADEMARK OFFICE
CERTIFICATE OF CORRECTION

PATENT NO. : 5,648,374
DATED : July 15, 1997
INVENTOR(S) : A. Cordi; J-M Lacoste; M. Laubie; T. Verbeuren; J-J Descombes; M. Millan It is certified that error appears in the above-indentified patent and that said Letters Patent is hereby corrected as shown below:

Column 16, line 26: "A compound of selected from those claim 1, wherein Y" should read -- A compound of claim 1, selected from those wherein Y --.

Signed and Sealed this

Fourteenth Day of October, 1997

Attest:

BRUCE LEHMAN

Attesting Officer

Commissioner of Patents and Trademarks